United States Patent
Matula

[19]

[11] Patent Number: 6,125,688
[45] Date of Patent: Oct. 3, 2000

[54] METHOD OF DETERMINING PULP PROPERTIES

[75] Inventor: Jouni Matula, Savonlinna, Finland

[73] Assignee: Andritz-Ahlstrom Oy, Espoo, Finland

[21] Appl. No.: 09/341,187

[22] PCT Filed: Feb. 17, 1998

[86] PCT No.: PCT/FI98/00142

§ 371 Date: Jul. 6, 1999

§ 102(e) Date: Jul. 6, 1999

[87] PCT Pub. No.: WO98/37402

PCT Pub. Date: Aug. 27, 1998

[30] Foreign Application Priority Data

Feb. 18, 1997 [FI] Finland ..................... 970671

[51] Int. Cl.$^7$ ................ G06F 15/46; G01B 21/02; G01N 7/14; G01N 33/16

[52] U.S. Cl. ............ 73/19.01; 73/99.05; 73/53.03; 422/68.1; 422/92

[58] Field of Search .................. 73/19.01, 19.05, 73/19.1, 53.03, 19.09, 599, 64.53; 422/68.1, 92

[56] References Cited

U.S. PATENT DOCUMENTS

| | | | |
|---|---|---|---|
| 4,164,137 | 8/1979 | Williamson | 73/19 |
| 4,184,359 | 1/1980 | Gracey | 73/19 |
| 4,329,869 | 5/1982 | Toda | 73/19 |
| 4,584,866 | 4/1986 | Janssen | 73/19 |
| 4,700,561 | 10/1987 | Dougherty | 73/19 |
| 4,730,493 | 3/1988 | Lebaud et al. | 73/599 |
| 4,758,408 | 7/1988 | Krawetz et al. | 422/92 |
| 4,862,729 | 9/1989 | Toda et al. | 73/19 |
| 4,924,695 | 5/1990 | Kolpak | 73/61.1 R |
| 5,041,990 | 8/1991 | Yabumoto et al. | 364/510 |
| 5,220,513 | 6/1993 | Seiden et al. | 364/500 |
| 5,243,848 | 9/1993 | Cox et al. | 73/19.05 |
| 5,285,674 | 2/1994 | Strub | 73/19.01 |
| 5,400,641 | 3/1995 | Slemon et al. | 73/19.01 |
| 5,442,948 | 8/1995 | Cowing | 73/19.05 |
| 5,621,161 | 4/1997 | Leyse | 73/19.01 |
| 5,653,250 | 8/1997 | Sigmund et al. | 137/7 |
| 5,932,792 | 8/1999 | Dougherty | 73/19.01 |

FOREIGN PATENT DOCUMENTS

| | | |
|---|---|---|
| 23 62 158 | 1/1975 | Germany . |
| 25 14 625 | 10/1975 | Germany . |
| 3210591A | 10/1983 | Germany . |
| 3421176A | 12/1985 | Germany . |
| 43 22 017 | 1/1995 | Germany . |
| 4435594 | 4/1996 | Germany . |
| 960574A | 9/1982 | U.S.S.R. . |

*Primary Examiner*—Hezron Williams
*Assistant Examiner*—J. David Wiggins
*Attorney, Agent, or Firm*—Nixon & Vanderhye P.C.

[57] ABSTRACT

The present invention is related to a method of determining the amount of gas in a liquid. The method is particularly well suited for determining the amount of both the gas in the form of bubbles and the gas dissolved in pulp, i.e. in various fiber suspensions of paper and pulp industry. The invention is advantageously applied to the control and regulation applications of removal of air in the short circulation of a paper machine.

21 Claims, 2 Drawing Sheets

METHOD OF DETERMINING PULP PROPERTIES

CROSS REFERENCE TO RELATED APPLICATION

This application is the U.S. National Phase of PCT/FI98/00142 filed Feb. 7, 1998.

The present invention relates to a method for determining the amount of gas contained in liquid. The method according to the invention is particularly well applicable in determining of the amount of gas, both in the form of bubbles and in dissolved state, contained in the various fiber suspensions, i.e. pulps, of the pulp and paper industry. The invention is advantageously applied in control and regulation systems of degassing in the short circulation of a paper machine.

The pulp used in the manufacture of paper, which is normally supposed to contain water, brushed out fibers and required additives, also contains air and other gases depending on the apparatus, the processes and the grade of pulp.

Air entrains into the pulp with high-consistency pulp, circulation waters, pulping and mixing. Also leaking vacuum seals and open turbulent flows introduce air into the process. Chemical and microbiological reactions release gases in the pulp, the most common gas being $CO_2$. Also other gases may be present such as $O_2$, $SO_2$, $H_2S$, and $Cl_2$.

Gas exists in the pulp in two basic forms: as bubble-formed air and as dissolved gas. Bubble-formed air may be divided into free and residual air. Free air means air bubbles moving freely in the liquid between fibers. Residual air is formed when free air is dispersed mechanically for example in a grinder. Microbubbles produced in this way adhere firmly to the surface of the fibers or to the lumen. Dissolved gases constitute various gases dissolved in the liquid, for example $CO_2$ $O_2$, $N_2$, etc. In this form, gases usually do not cause problems and they do not affect the pulp properties but, due to changes in the pressure, the temperature or the chemical balance, dissolved gases may turn into bubbles. The total volume of air varies greatly depending on conditions and the grade of pulp. For example in the head box feed flow, there is normally 1–4% by volume of air.

The most visible influence of air in the paper machine is froth and air bubble on the wire generated by free air. Air in the form of bubbles cause fluctuations in the consistency as air bubbles present in the pulp displace by their volume fibers and water. Residual air has the most significant influence on the pulp properties and the quality of paper. Fibers which contain much residual air are thickened onto an open surface. While moving the fibers bump and adhere to each other. Residual air impedes the operation of a paper machine and degrades the paper quality.

Disturbances caused by air may be avoided by carefully designing the apparatus and processes to prevent air from being mixed into the pulp and/or by removing air entrained in the pulp. Air may be removed advantageously by a DECULATOR® degassing apparatus by Ahlstrom Machinery Corporation.

A large number of different apparatus, ways and methods for determining the amount of gas present in liquid, both in a dissolved and a gaseous state exist.

DE-B-23 62 158 relates to measuring the amount of gas dissolved in liquid by means of subatmospheric pressure. According to the method of the publication, the sample vessel consisting of a lower container having a pressure air chamber disposed therein and of a measuring tube disposed in the upper portion of the container is filled with the liquid to be measured and the end of the measuring tube is closed. Subsequently, air is withdrawn from the pressure air chamber so as to created a slight subatmospheric pressure in the measuring tube. Due to the subatmospheric pressure, gas is separated from the liquid and the liquid level in the measuring tube decreases indicating the amount of the separated gas. According to the publication, this measurement must be repeated a few times to find out the true volume of gas dissolved in the liquid.

U.S. Pat. No. 4,329,829 relates to measuring the amount of gas bubbles contained in liquid. According to the method described in the publication, a sample of liquid is introduced into a container and it is pressed under two different pressures; between the pressing actions the pressure of the sample is relieved to be atmospheric. The two volume changes are registered and the amount of gas in bubble form in the liquid is calculated according to Boyle's law.

U.S. Pat. No. 4,862,729 relates to an improvement of the method of the above US publication and deals with measuring gas amounts which are small and easily soluble in liquid. According to the method of the publication, a sample of liquid is introduced into a measuring chamber, the volume of the chamber is increased to two different volumes and the corresponding pressures are measured, relieving the pressure of the sample between the measurements to be atmospheric. The amount of gas dissolved in the liquid may be determined based on Boyle's law. The publication states further that separation of the dissolved gas is slow.

U.S. Pat. No. 4,700,561 relates to an automatic on-line gas amount measuring apparatus. According to the publication, a sample of liquid is collected to a cylinder, the liquid in the cylinder is subjected to pressure and by determining the change of volume caused by the pressure change, the amount of gas may be calculated based on Boyle's law. The publication concentrates to a large extent on the structures and operations required by the automation of the measuring apparatus.

DE-A-43 22 017 deals primarily with determination of the carbon dioxide content of soft drinks. In other words, it relates to determining the amount of gas dissolved in liquid. The publication discloses how the separation speed of the gas dissolved in liquid may be substantially increased for example by means of ultrasound.

However, the measuring methods described in all the above publications have one drawback. All the publications deal with determining the amount of either gas dissolved in liquid or gas in bubble form present in the liquid. None of them suggests determining the amount of both dissolved gas and bubble-formed gas during the same measuring operation. Measurement of this kind is, however, essentially important in many fields of industry. For example, in the pulp and paper industry, it is of primary importance to know the volume of gas in the bubble form and the volume of dissolved gas in the liquid as bubble-formed gas may as such cause foaming and other problems.

Further, as far as the pressure of the process remains unchanged or increases, the gas dissolved in the liquid does not cause problems but when the process pressure drops the gas dissolved in the liquid accumulates into bubbles and in favourable conditions creates for example foam.

The main object of the present invention is to provide an improved method, when compared with prior art methods, for measuring bubble-formed air and dissolved gases in the pulp.

A method according to a preferred embodiment of the invention reaching the above objective comprises the following stages:

a) liquid to be studied is introduced into a measuring container;

b) the liquid in the rest state ($V_0$, $p_0$) is subjected to superatmospheric pressure pi whereby its volume decreases by $V_1$;

c) the amount of gas in bubble form is determined based on the volume change $V_1$ caused by the pressure change $p_1$;

and is characterized in that d) the liquid in the measuring container is released to its rest state ($V_0$, $p_0$);

e) subatmospheric pressure $p_2$ is applied to the liquid in the rest state ($V_0$, $p_0$) in the container whereby the subatmospheric pressure $P_2$ releases at least part of the dissolved gas to bubble form and the volume increases by $V_2$;

f) the amount of gas dissolved in liquid is determined at least by means of the volume changes $V_1$ and $V_2$.

The method according to the invention is illustrated in detail in the appended drawing figures

DETAILED DESCRIPTION OF THE DRAWINGS

Figure 1:
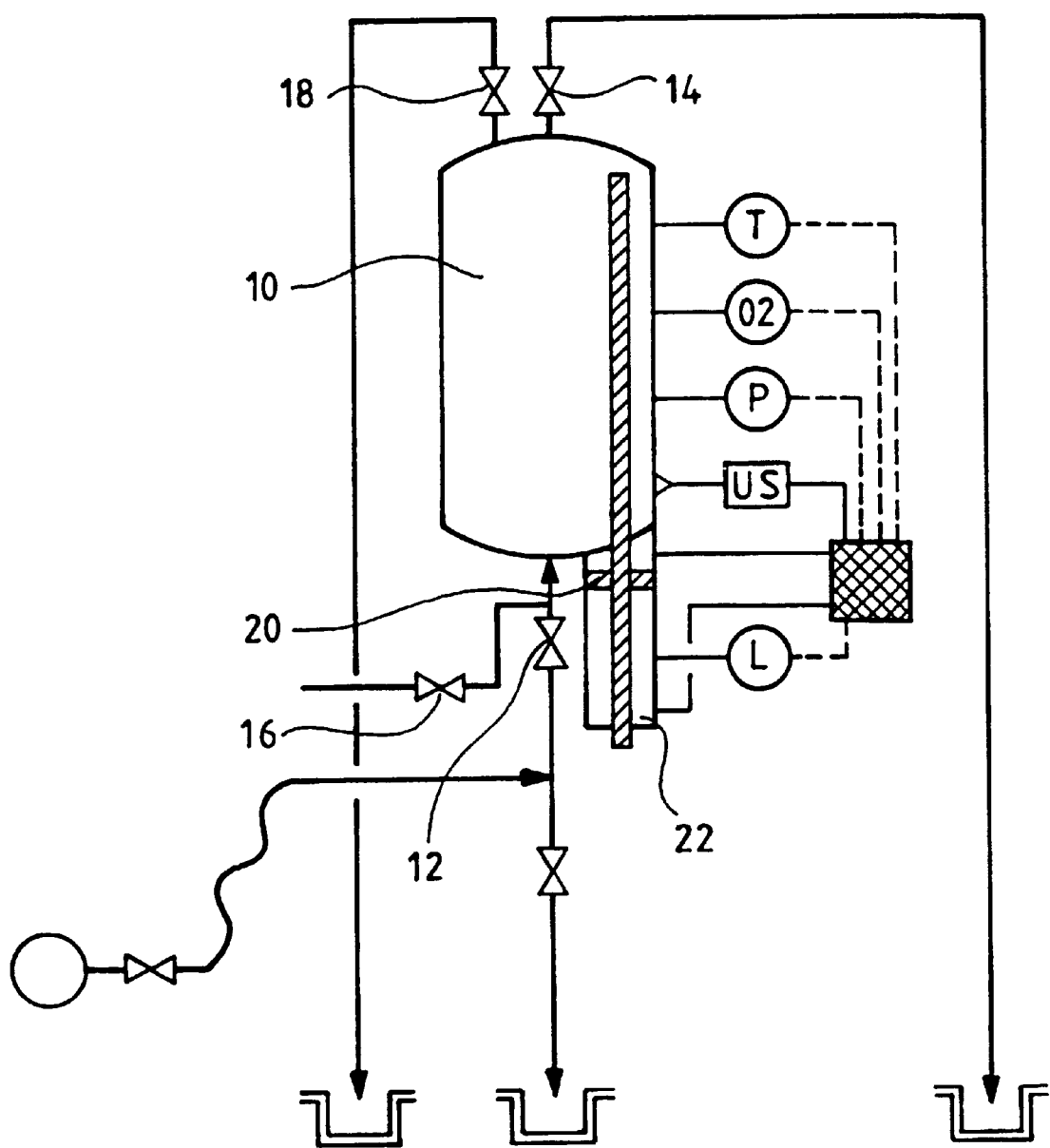
FIG. 1 illustrates schematically a preferred embodiment of the invention.

FIG. 1 illustrates a measuring system according to the invention. Probes for measuring at least the temperature T, the pressure p and the dissolved gas, for example oxygen $O_2$, have been provided in a measuring container 10. Further, the measuring container has been provided with an ultrasonic detector US and apparatus L for determining the movement of a piston 20 in a cylinder 22 annexed to the measuring container. The measuring container 10 has also valves 12, 14, 16 and 18 for at least supply and discharge of pulp, and supply and discharge of flushing water, respectively. Thus, after the measuring has been completed the measuring container may be drained and flushed. If desired, the whole measuring operation may be automated.

The measuring apparatus according to the present invention may be used to measure air and gases either at atmospheric pressure or at the pressure of the process. The measurement at the atmospheric pressure may be arranged to take place automatically for example so that while the pulp to be measured flows in a smooth flow through the measuring container 10, a push on a measuring button closes the feed valve of the apparatus and after a delay also the discharge valve which ensures that the pressure in the measuring container 10 has stabilized. The volume defined by the valves is predetermined precisely and known by the processor of the apparatus so that the influence of the position of the piston 20 on the volume may be determined. At the process pressure, the measurement is performed so that the push on the measuring button closes the discharge valve of the apparatus and after a delay also the feed valve. Then an accurately known volume, at the process pressure, is retained between the valves.

The apparatus works in principle so that movement of the piston 20 in the cylinder 22 changes the volume of the measuring container-cylinder combination. Pressing the piston 20 from the rest state, i.e. volume $V_0$, pressure $p_0$, deeper into the cylinder 22 (i.e. in the figure upwards) the pressure in the measuring container 10 increases and the volume of the entire measuring container-cylinder combination decreases when the gas in bubble form is compressed. A preferred method of performing the measurement is to push the piston into the cylinder until the pressure has reached a desired reading $p_1$, for example 50 kPa superatmospheric pressure, after which the measuring device registers the volume change $V_1$ in the measuring container-cylinder combination based on information given by the piston position probes. With this information the amount of bubble-formed gas in the pulp may be calculated according to Boyle's law.

Figure 2:
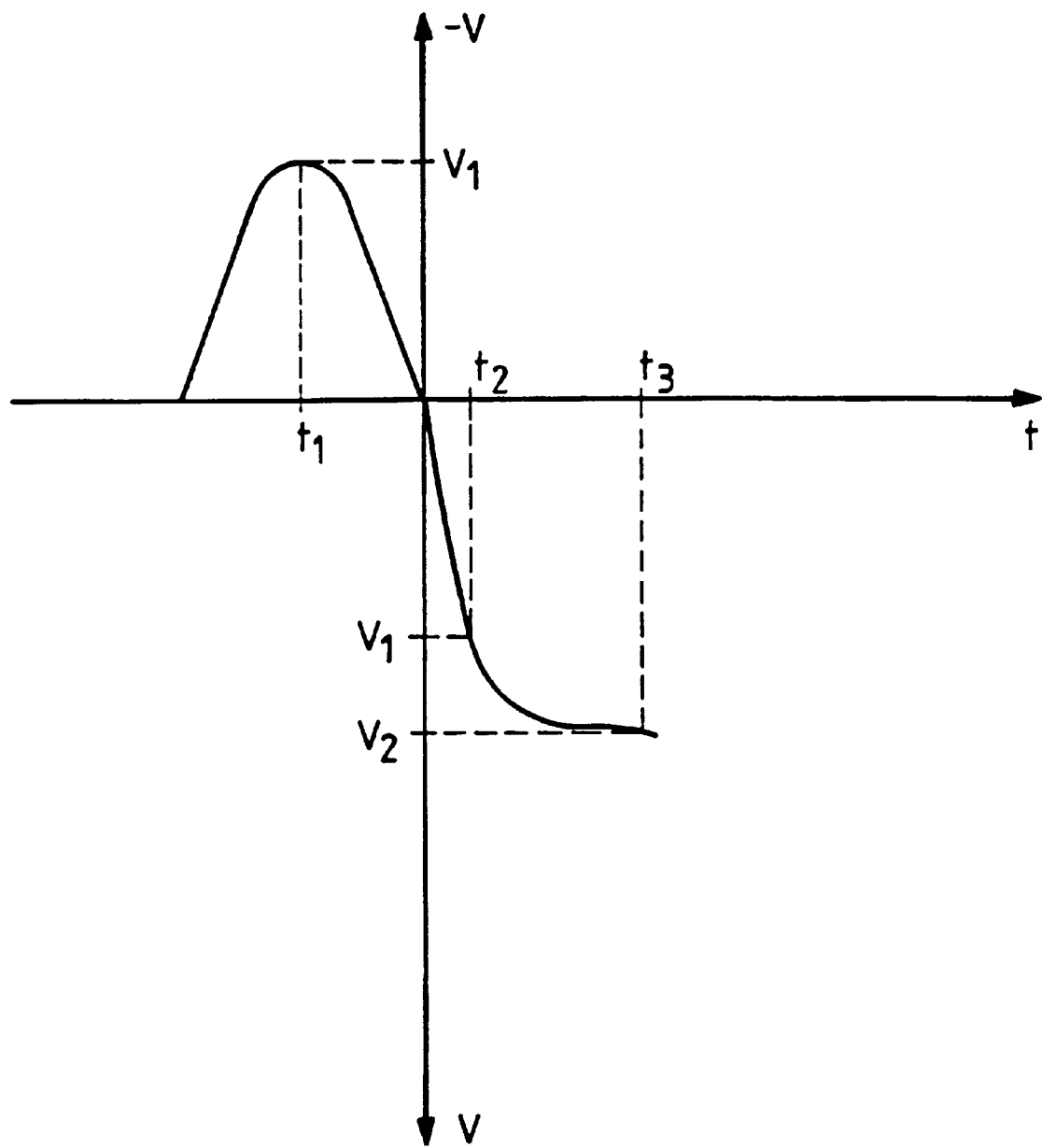
FIG. 2 illustrates schematically a measuring arrangement for carrying out an embodiment of the method according to the invention.

The measuring pressure $p_1$ used should preferably be fairly low in order to avoid causings gas in bubbles to be dissolved into the liquid. According to a preferred embodiment of the invention, measuring of the amount of dissolved gas is started by pulling the piston 20 from the rest position in the cylinder 22 outwards (in the figure downwards) so that the volume of the measuring container increases by $V_1$ measured from the rest state. Then the pressure in the measuring container-cylinder combination decreases to $-p_1$, for example 50 kPa subatmospheric pressure (corresponding to the superatmospheric pressure used in the measurement of the bubble-formed gas) and the dissolved gas tends to be separated into bubbles. FIG. 2 demonstrates most concretely the measurement, depicting the volume change as a function of time. The figure indicates that the volume decreases from the rest state by VI when the piston is pressed into the cylinder with a given pressure (for example 50 kPa). Correspondingly, the volume increases from the rest state by $V_1$ when the pressure is reduced to a corresponding subatmospheric pressure $p_1$, ($-50$ kPa) in the measuring container 10. When the same subatmospheric pressure $p_1$ is maintained for a longer time in the measuring container the piston 22 moves gradually further outwards (to the reading $V_2$) which means that dissolved gas has been separated from the pulp in the measuring container 10 into bubbles. By determining the change of volume $V_2-V_1$ caused by the separation of dissolved gas, the share of the dissolved gas may be determined by means of pressure for example according to Boyle's law (in the general form $p*V/T$=constant, and when the temperature is constant, $p*V$=constant).

Another way of performing the measurement is to use different pressures. In other words, the superatmospheric pressure used in the determining of the bubble-formed gas may be for example 50 kPa and the subatmospheric pressure used in the determining of the dissolved gas for example $-70$ kPa. In this case, the determining of the volume of the bubble-formed gas performed at superatmospheric pressure is done by registering the pressure $p_1$ and the volume change $V_1$ and the amount $M_1$ of the bubble-formed gas is determined using these readings and according to Boyle's equation. Subsequently, the sample is returned to its initial state, volume $V_0$, pressure $p_0$, and after that the same sample is subjected to a desired subatmospheric pressure $p_2$, whereby the change of volume will be $V_2$. These pressure and volume readings are used to further determine by means of Boyle's law the total amount $M_2$ of the gas separated from the sample whereby $M_2$ contains both the bubble-formed and the dissolved gas. When the amount of the bubble-formed gas is known to be $M_1$, the amount of the dissolved gas may be calculated by subtraction $M_2-M_1$. As it is usually desirable to express the gas volume as a percentage, this should be calculated separately.

As particularly the measuring of dissolved gas may be slow the measuring device may be provided with an ultrasonic vibrator. During the relatively strong cavitation-like vibration caused by the ultrasound the releasing speed of the dissolved gases into bubbles is multiplied and the measuring time is correspondingly shorter. In automatic measuring, the measuring of the dissolved gas is stopped after a predetermined time t and the amount of the released gas is calculated according to Boyle's law.

Subsequently, the piston is returned to its initial position and a new measurement may be started. When the measuring device is used to continuously monitor the process the interim period between the measurements is set as required. Efficient operation of the measuring device prefers as short interim periods as possible. In automatic operation, the measurement is preferably repeated every 5–10 minutes.

A measuring device for dissolved oxygen or a corresponding gas may also be connected to the measuring device. The device measures the true amount of the dissolved gas or the amount in percentage.

According to a preferred embodiment of the present invention, measuring probes T and P for momentary measuring of the temperature and the pressure of the pulp have been connected to a device for measuring the bubble-formed and the dissolved gas. Several measuring members measuring the temperature and the pressure and the position of the precision piston required for the determining of the gas amount may be disposed in the process to be monitored. In this way, the monitoring of the pulp properties becomes remarkably more efficient.

Further, is should be noted that when the amount of dissolved gas is determined in most cases in each point from liquids or fiber suspensions of very similar type the measuring may be accelerated as follows. When the measuring is started, the volume of dissolved gas is determined as accurately as possible in each point for example by using much time for performing each measurement, possibly also by using an ultrasound vibrator. By determining the separation speed of the dissolved gas, i.e. observing as a function of time how fast gas is separated (this may be illustrated graphically for example by a curve drawn in a coordinate system the axes of which are the volume of the separated gas in percent and the time it is possible to predict the amount of gas in a liquid even on the bases of a very short measuring time. In other words, the observation of the separation speed may give a result according to which 90% of the total gas volume is separated from a certain liquid in certain conditions in ten minutes and half of the total gas volume is separated in two minutes. Then the further measurements may be performed in two minute periods and the curves may be used to determine the true volume of dissolved gas. When a microprocessor or a computer is used to process the measuring results, the data from the inspection of the separation speed of dissolved gas in a large number of different liquids in different conditions may be input into the computer and thus even changes in conditions do not slow down the measurements in the mill. It is even possible to record into the processor/the computer of the device data on the separation speed of various liquids in various conditions obtained in laboratory conditions in advance before the device is brought to the mill which allows the device to be used at once from the beginning quickly and in a practical way.

As is disclosed by the above examples the invention solves the problem of determining the volume of the gas dissolved in pulp, which has not been solved before. The method of the present invention is able to determine the amount of the dissolved gas with an accuracy which is adequate for most purposes. Further, the measuring of the amount of the dissolved gas may be accelerated by employing an ultrasonic vibrator and thus the degassing of the short circulation may be controlled better and thereby paper of higher quality may be produced. Also, it should be noted that, in addition to the short circulation of paper manufacture, the invention may be applied in feed pumps, screens, washers etc. of a pulp production process or in general, in the parts of the pulp production process in which measuring of air volumes is necessary. The examples described above do in no way intend to limit the invention from what has been defined in the appended patent claims.

As the above description discloses, a method of measuring gas volumes has been developed which is remarkably more efficient, more accurate and simpler than prior art methods. Further, the method of the invention may be provided to pay attention to temperature variations either by performing temperature calibration mathematically based on the data obtained from the temperature probes or by arranging a constant temperature in the measuring container. It should be noted that the measuring method of the invention has been described above by way of example, only, and the real scope of protection of the invention is defined by the appended patent claims, alone.

We claim:

1. A method of determining the amount of both bubbles and dissolved state gas in paper pulp in the short circulation of a paper machine, using a container with an adjustable volume, comprising sequentially:
   (a) introducing a paper pulp sample having both bubbles and dissolved state gas into the container to establish a rest state, $V_p$, $p_0$ of the paper pulp in the container;
   (b) subjecting the paper pulp sample in the rest state to a superatmospheric pressure $p_1$ greater than $p_0$, so as to cause the volume in the container to decrease by $V_1$;
   (c) after (b) determining the amount of gas in bubbles from the volume change $V_1$ based upon the increase in pressure to $p_1$;
   (d) subjecting the paper pulp sample in the container at the rest state to a subatmospheric pressure $p_2$ lower than $p_0$, so as to release at least part of the dissolved gas into bubbles and to increase the volume by $V_2$; and
   (e) determining the amount of dissolved gas in the paper pulp sample by utilizing the volume changes $V_1$ and $V_2$.

2. A method as recited in claim 1 wherein (d) and (e) are practiced after the paper pulp sample has come to rest state after (b).

3. A method as recited in claim 2 wherein (e) is practiced by using $p_2$ substantially equal to $p_1$; and wherein (e) is practiced by determining $V_2-V_1$.

4. A method as recited in claim 3 wherein (e) is further practiced by utilizing the time spent to effect the volume change $V_2-V_1$ to determine the amount of gas released.

5. A method as recited in claim 4 wherein (e) is further practiced by utilizing the value of $p_1$ to determine the amount of dissolved gas released.

6. A method as recited in claim 1 further comprising measuring the pressure and temperature of the liquid sample during (b) and (d).

7. A method as recited in claim 1 wherein (d) is further practiced to measure the release speed of the gas bubbles, and wherein measurement thereof is stopped when the release speed clearly decelerates, and wherein (e) is practiced utilizing the result from (d).

8. A method as recited in claim 1 wherein (d) and (e) are practiced a plurality of times for a given paper pulp sample.

9. A method as recited in claim 8 wherein the container is capable of a maximum subatmospheric pressure; and wherein the last of the plurality of times (d) is practiced where $p_2$ substantially equals the maximum subatmospheric pressure the container is capable of.

10. A method as recited in claim 1 wherein (b) and (d) are practiced by moving a piston within the container.

11. A method as recited in claim 1 further comprising subjecting the pulp to ultrasound treatment during the practice of (d).

12. A method as recited in claim 1 further comprising, after (a)–(e) are completed, draining the container of the pulp sample and flushing the container, and then repeating (a)–(f) with another sample.

13. A method as recited in claim 12 wherein (a) is practiced at an interval of less than about ten minutes.

14. A method as recited in claim 1 further comprising determining the oxygen content of the dissolved gas.

15. A method as recited in claim 1 wherein (a)–(e) are practiced at a substantially constant temperatures.

16. A method as recited in claim 1 wherein (a) and (d) are practiced so that the rest pressure $p_0$ is substantially atmospheric pressure.

17. A method as recited in claim 1 wherein (b) and (d) are practiced so that the maximum deviation from atmospheric pressure is about 70 kPa.

18. A method as recited in claim 2 wherein (e) is practiced to determine the amount of both the bubble formed gas and the dissolved gas based upon the volume $V_2$ and the pressure $p_2$; and wherein the amount of dissolved gas is further determined by subtracting the amount of bubble formed gas determined in (c).

19. A method of determining the amount of both bubbles and dissolved state gas in a liquid, using a container with an adjustable volume, comprising:

(a) introducing a liquid sample having both bubbles and dissolved state gas into the container to establish a rest state, $V_0$, $p_0$ of the liquid in the container;

(b) subjecting the liquid sample in the rest state to a superatmospheric pressure $p_1$ greater than $p_0$, so as to cause the volume in the container to decrease by $V_1$;

(c) after (b) determining the amount of gas in bubbles from the volume change $V_1$ based upon the increase in pressure to $p_1$;

(d) subjecting the liquid sample in the container at the rest state to a subatmospheric pressure $p_2$ lower than $p_0$, so as to release at least part of the dissolved gas into bubbles and to increase the volume by $V_2$;

(e) after (b) and (d) determining the amount of dissolved gas in the liquid sample by utilizing the volume changes $V_1$ and $V_2$; and wherein (d) is further practiced to measure the release speed of the gas bubbles, and wherein measurement thereof is stopped when the release speed clearly decelerates, and wherein (e) is practiced utilizing the result from (d).

20. A method of determining the amount of both bubbles and dissolved state gas in a liquid, using a container with an adjustable volume, comprising:

(a) introducing a liquid sample having both bubbles and dissolved state gas into the container to establish a rest state, $V_0$, $p_0$ of the liquid in the container;

(b) subjecting the liquid sample in the rest state to a superatmospheric pressure $p_1$ greater than $p_0$, so as to cause the volume in the container to decrease by $V_1$;

(c) after (b) determining the amount of gas in bubbles from the volume change $V_1$ based upon the increase in pressure to $p_1$;

(d) subjecting the liquid sample in the container at the rest state to a subatmospheric pressure $p_2$ lower than $p_0$, so as to release at least part of the dissolved gas into bubbles and to increase the volume by $V_2$;

(e) after (b) and (d) determining the amount of dissolved gas in the liquid sample by utilizing the volume changes $V_1$ and $V_2$; and wherein (d) is further practiced to measure the release speed of the gas bubbles, and wherein measurement thereof is stopped when the release speed clearly decelerates, and wherein (e) is practiced utilizing the result from (d), and wherein the container is capable of a maximum subatmospheric pressure; and wherein the last of the plurality of times (d) is practiced where $p_2$ substantially equals the maximum subatmospheric pressure the container is capable of.

21. A method of determining the amount of both bubbles and dissolved state gas in a liquid, using a container with an adjustable volume, comprising:

(a) introducing a liquid sample having both bubbles and dissolved state gas into the container to establish a rest state, $V_0$, $p_0$ of the liquid in the container.

(b) subjecting the liquid sample in the rest state to a superatmospheric pressure $p_1$ greater than $p_0$, so as to cause the volume in the container to decrease by $V_1$;

(c) after (b) determining the amount of gas in bubbles from the volume change $V_1$ based upon the increase in pressure to $p_1$;

(d) subjecting the liquid sample in the container at the rest state to a subatmospheric pressure $p_2$ lower than $p_0$, so as to release at least part of the dissolved gas into bubbles and to increase the volume by $V_2$;

(e) after (b) and (d) determining the amount of dissolved gas in the liquid sample by utilizing the volume changes $V_1$ and $V_2$; and wherein (b) and (d) are practiced so that the maximum deviation from atmospheric pressure is about 70 kPa.

\* \* \* \* \*